(12) United States Patent
Pryor

(10) Patent No.: US 11,931,014 B2
(45) Date of Patent: Mar. 19, 2024

(54) URINE CAPTURING DEVICE HAVING A SPLASHGUARD AND METHODS OF USING THEREOF

(71) Applicant: Monya Faye Pryor, Hendersonville, TN (US)

(72) Inventor: Monya Faye Pryor, Hendersonville, TN (US)

( * ) Notice: Subject to any disclaimer, the term of this patent is extended or adjusted under 35 U.S.C. 154(b) by 778 days.

(21) Appl. No.: 16/505,018

(22) Filed: Jul. 8, 2019

(65) Prior Publication Data

US 2021/0007719 A1 Jan. 14, 2021

(51) Int. Cl.
| | | |
|---|---|---|
| *A47K 11/00* | (2006.01) | |
| *A47K 11/06* | (2006.01) | |
| *A61B 10/00* | (2006.01) | |
| *A61G 9/00* | (2006.01) | |

(52) U.S. Cl.
CPC ............ *A61B 10/007* (2013.01); *A47K 11/06* (2013.01); *A61G 9/006* (2013.01); *A61B 2560/0406* (2013.01)

(58) Field of Classification Search
CPC .......... A61B 10/007; A61B 2560/0406; A61B 2560/06; A47K 11/06; A61F 5/451; A61F 5/453; A61F 5/455; A61F 5/4556; A61F 2560/06; A61G 9/00
See application file for complete search history.

(56) References Cited

U.S. PATENT DOCUMENTS

| | | | |
|---|---|---|---|
| 1,657,975 A | 1/1928 | Shiells | |
| 1,928,170 A | 9/1933 | Dwork | |
| 2,182,254 A | 12/1939 | Farrell | |
| 2,195,156 A | 3/1940 | Steward | |
| 2,358,850 A | 9/1944 | Chenault | |
| 2,359,830 A | 10/1944 | Deckert | |
| 2,491,799 A | 12/1949 | Clarke | |
| 3,095,578 A | 7/1963 | Stanford | |
| 3,444,563 A | 5/1969 | Gordon, Jr. | |
| 3,992,729 A | 11/1976 | Mills | |
| 4,531,245 A | 7/1985 | Lowd | |
| 4,771,484 A | 9/1988 | Mozell | |
| 5,331,689 A | 7/1994 | Haq | |
| D370,975 S | 6/1996 | Mohr | |
| 5,819,334 A | 10/1998 | Maze | |
| 5,920,916 A | 7/1999 | Norton | |
| 6,183,454 B1 * | 2/2001 | Levine | A61F 5/4556 604/355 |

(Continued)

FOREIGN PATENT DOCUMENTS

| | | | | |
|---|---|---|---|---|
| CN | 108784750 A | * | 11/2018 | ........... A61B 10/007 |
| CN | 109009238 A | * | 12/2018 | ........... A61B 10/007 |
| FR | 2786406 A1 | * | 6/2000 | ............. A61B 10/00 |

*Primary Examiner* — Daniel J Colilla

(74) *Attorney, Agent, or Firm* — Husch Blackwell LLP; Timothy L. Capria; Alexandra C. Lynn

(57) ABSTRACT

A device for capturing and disposing of urine comprises an elongated body. The elongated body includes a top surface, a groove disposed in the top surface, a bottom surface, a handle end, and a groin end opposite of the handle end. The device comprises an open neck in fluid communication with the aperture and extending away from the bottom surface. The device comprises a splashguard disposed at least partially around the aperture and extending away from the top surface. A container, such as a disposable bag, may be removably disposed on the open neck.

20 Claims, 6 Drawing Sheets

(56) References Cited

U.S. PATENT DOCUMENTS

| | | | |
|---|---|---|---|
| D467,338 S | 12/2002 | Rehrig | |
| 6,651,259 B1 | 11/2003 | Hartman | |
| 6,908,441 B1 * | 6/2005 | Bernard | A61B 10/007 600/574 |
| D607,995 S | 1/2010 | Miller | |
| 2002/0193762 A1 | 12/2002 | Suydam | |
| 2006/0111647 A1 * | 5/2006 | Starling | A61B 10/007 600/574 |
| 2009/0124929 A1 * | 5/2009 | Rossi-Pipitone | A61B 10/007 600/574 |
| 2016/0128524 A1 | 5/2016 | Poore | |
| 2017/0273818 A1 * | 9/2017 | Pryor | A61G 9/006 |

* cited by examiner

URINE CAPTURING DEVICE HAVING A SPLASHGUARD AND METHODS OF USING THEREOF

This is a Non-Provisional patent application filed by Monya Faye Pryor, a citizen of the United States, residing in Hendersonville, Tennessee for a "Urine Capturing Device Having a Splashguard and Methods of Using Thereof."

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF INVENTION

Urination is one of the most basic and essential of human functions. However, practical realities can pose many problems to the urination process for both men, women, and children.

Unsurprisingly given the involvement of the groin region, urination is very much a personal experience. Indeed, it is often difficult for those needing assistance from others with urination to accept such assistance. Moreover, these subjects, as well as those who have other complications (e.g., mobility problems) that make it more difficult for them to urinate by themselves and into traditional plumbed toilets, can desire to urinate less. These considerations may result in behavioral changes in the subject, such as a reduction of fluid intake in an attempt to urinate less often. However, a reduction in fluid intake can be deleterious to the health of the subject, resulting in symptoms in the subject ranging from headaches to decreased organ (e.g., kidney) function, pain, low blood pressure, and cramping, among others.

Furthermore, even healthy and mobile subjects may also attempt to prolong periods between urination and reduce fluid intake in an effort to urinate less frequently. Such individuals include professional transportation drivers, security personnel who are unable to leave a particular area, and even members of a family on a road trip. In addition to discomfort, these individuals may face risks associated with too little fluid intake or with infrequent urination (e.g., urinary tract infections).

What is needed, then, are devices that allow for convenient collection and storage of urine to allow subjects to urinate. Preferably, the devices will enable a subject to conveniently urinate in locations other than a bathroom. Preferably, the devices will enable a subject to urinate in a comfortable position, such as while seated in an upright position or in a low to high Fowler's position in a bed. Preferably, the devices will enable the subject to urinate without holding them in place once position or without the assistance of others.

BRIEF SUMMARY

The disclosed apparatus relates to a device for capturing and disposing of urine from the subject.

In one aspect, the device comprises an elongated body including a top surface, a handle end, and a groin end opposite of the handle end. The groin end may include a tapered profile and a curved edge.

The device comprises an open neck extending from the body in a direction away from the top surface. The open neck may be configured to securely receive a container.

The device comprises a groove disposed in the top surface along the elongated body. The device comprises an aperture disposed on the groove and in fluid communication with the open neck. The aperture may be configured to securely receive a removable stopper. The device may include a removable stopper configured to be received at least partially in the aperture. The groove is defined by a continuously curved indentation in the top surface. A top wall may be disposed around the groove.

The device comprises a splashguard extending from the top surface of the elongated body, the splashguard disposed at least partially around the aperture. The splashguard may include an inner width defined by a width of the groove. The splashguard may include an edge facing the groin end, the edge including a recess. The edge of the splashguard may curve inwardly or be tapered. The splashguard may have a hemispherical profile.

The device may comprise a sleeve extending around the open neck, the sleeve including one or more threads configured to operatively engage with one or more threads of a container. The sleeve may comprise an interior wall surface, and the one or more threads of the sleeve may be disposed around the interior wall surface. A gap may be disposed between the interior wall surface and the open neck.

A handle may curve outwardly from the handle end. The handle curves outwardly from the handle end. An opening may be disposed between the handle and the handle end. The elongated body of the top surface and a top surface of the handle may define a plane.

The device may include a bottom surface defined by a substantially flat plane.

It is therefore a general object of the current disclosure to provide a device for the capture of urine from a subject.

Another object of the current disclosure is to provide a device having a splashguard to prevent urine from escaping, or splashing out of, the device.

Yet another object of the invention is to provide a device for those who cannot or do not wish to urinate in a plumbed toilet or for those who have challenges (e.g., mobility) with urinating in a plumbed toilet.

DETAILED DESCRIPTION

Figure 1:
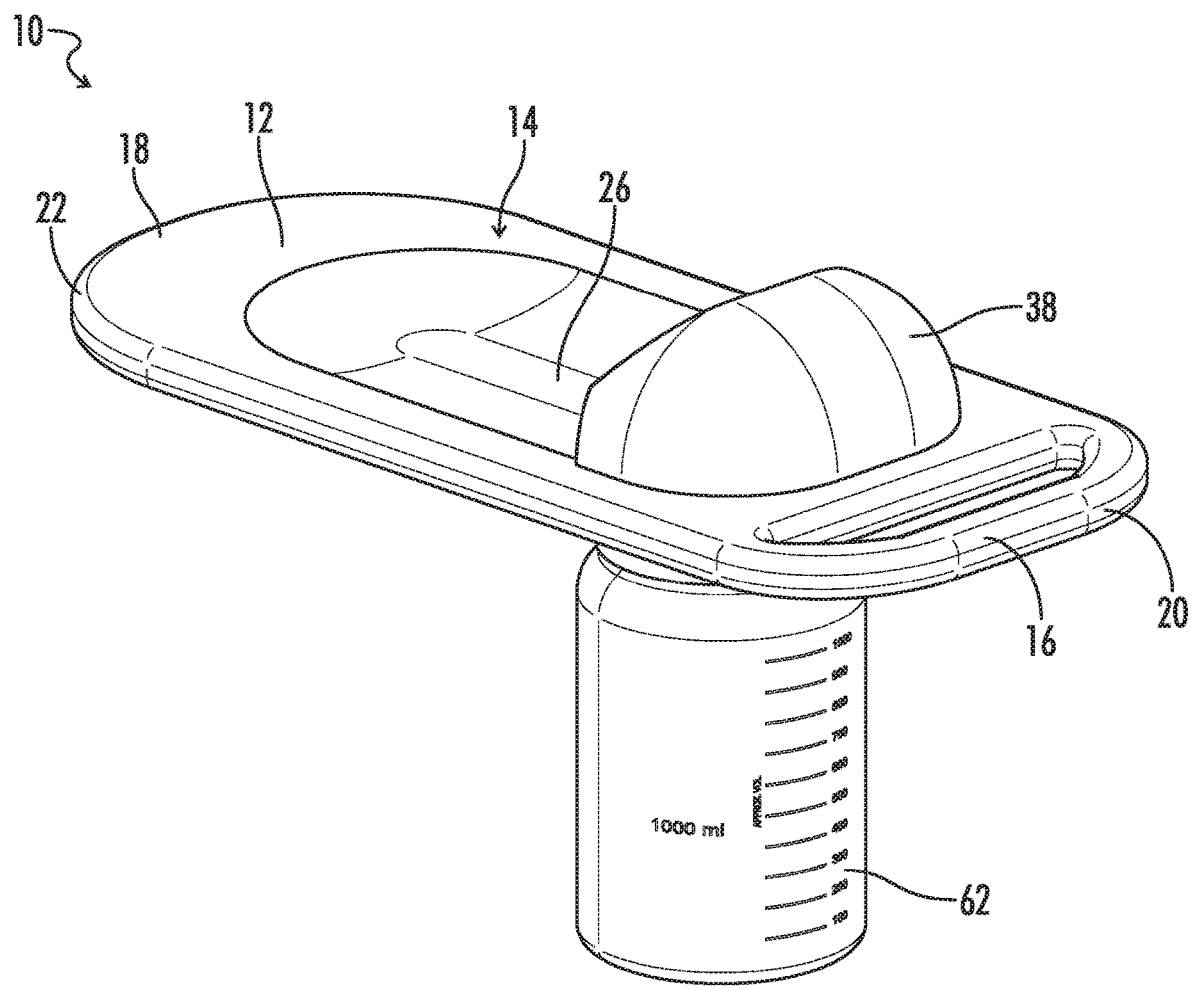
FIG. 1 illustrates a top perspective view of an embodiment of the device.
Figure 2:
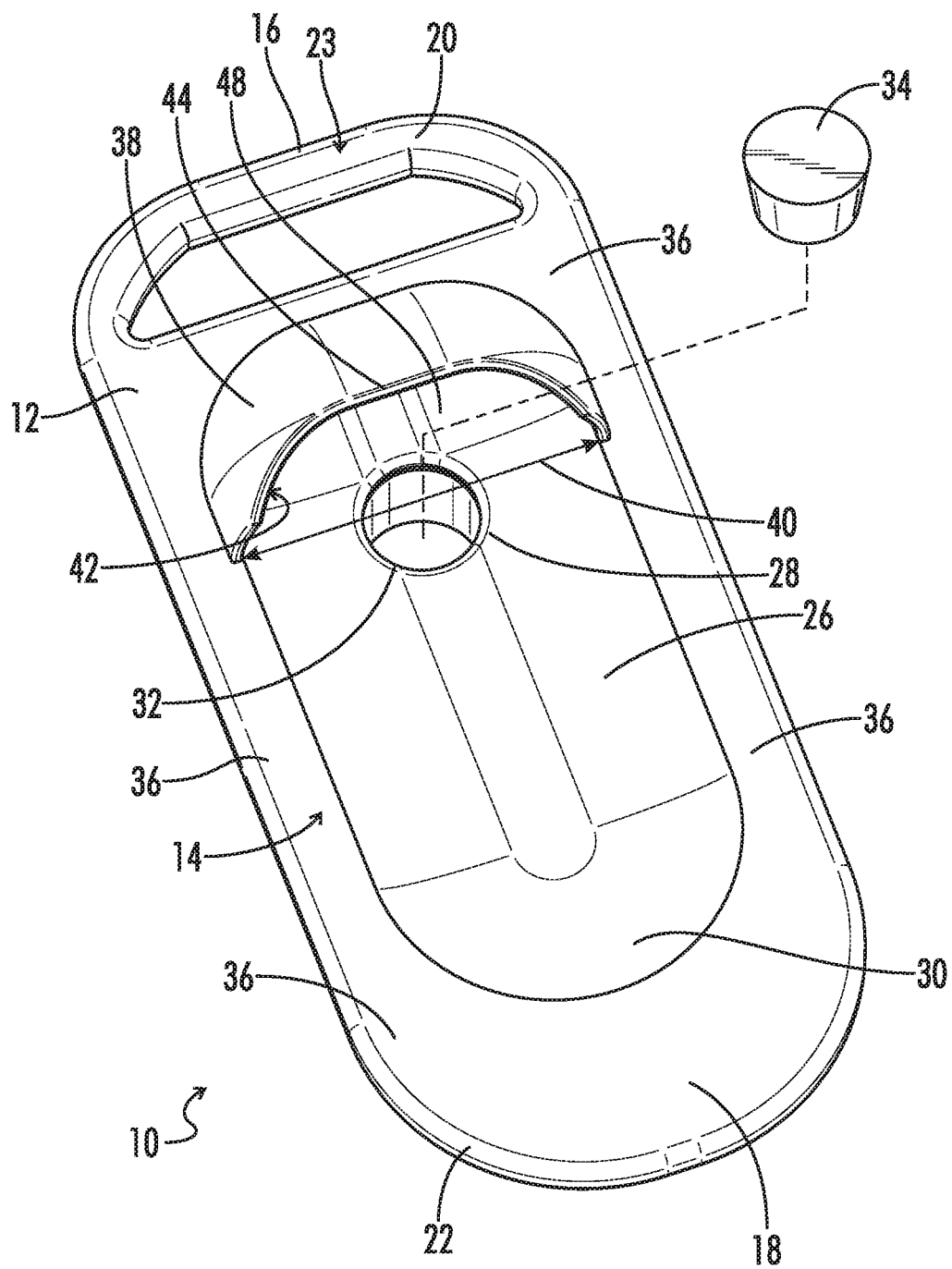
FIG. 2 illustrates a top view of the embodiment of FIG. 1.
Figure 3:
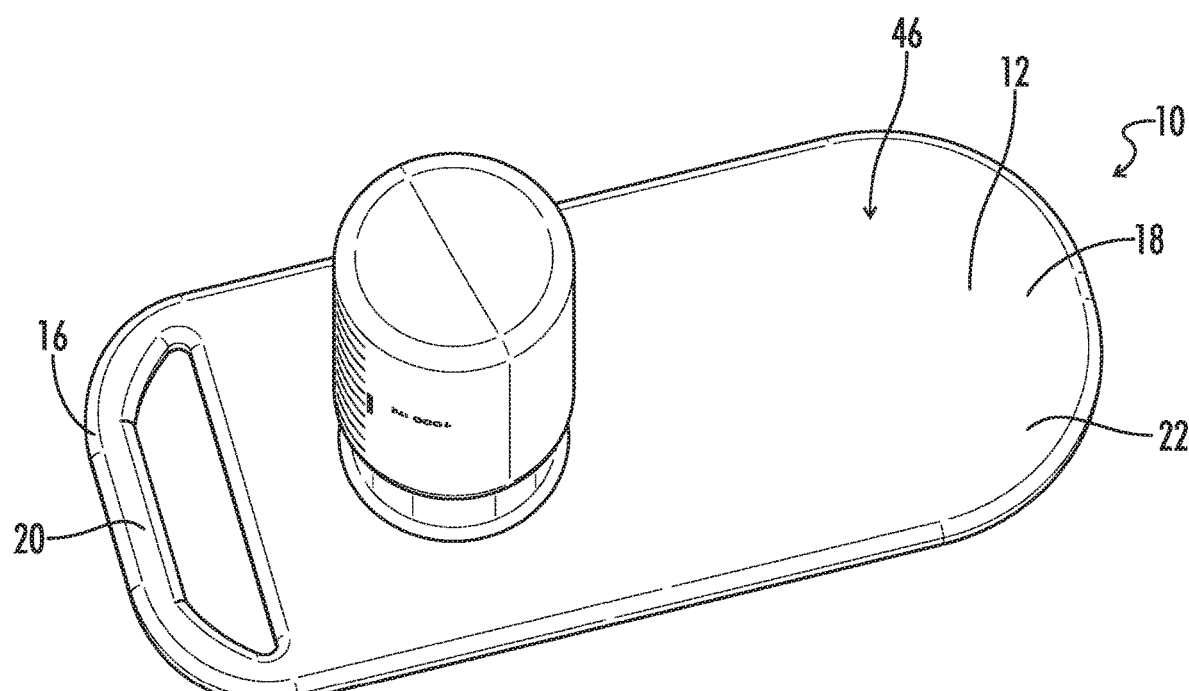
FIG. 3 illustrates a bottom view of the embodiment of FIG. 1.
Figure 4:
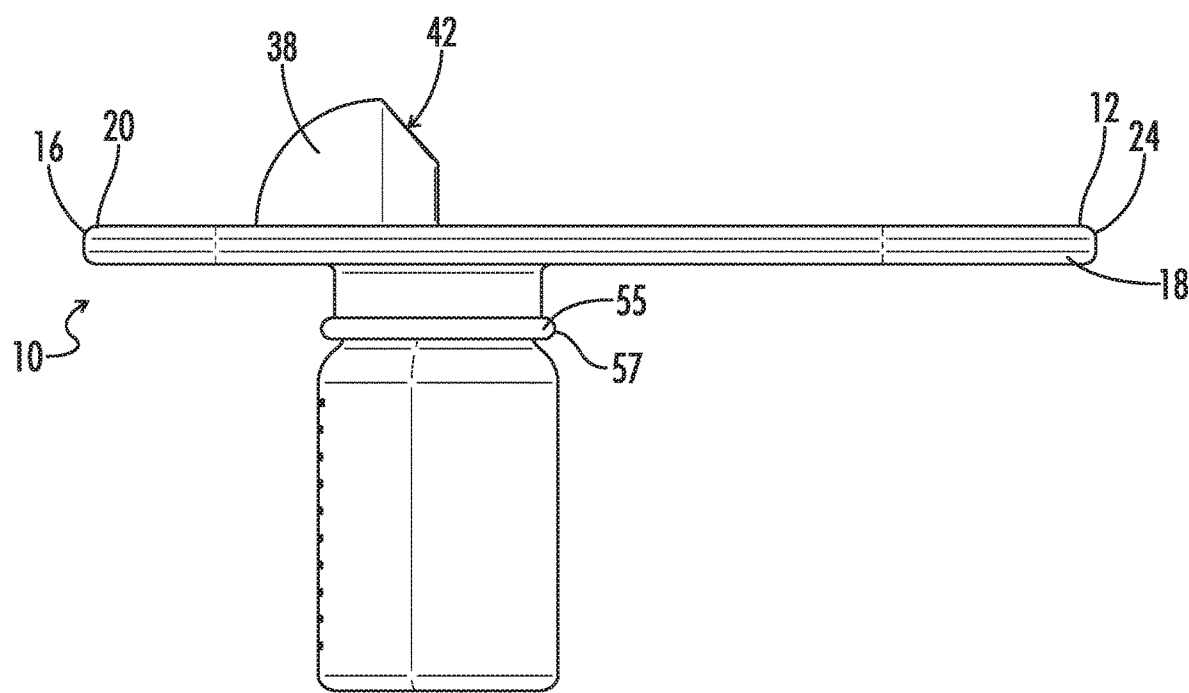
FIG. 4 illustrates an elevation view of the embodiment of FIG. 1.
Figure 5:
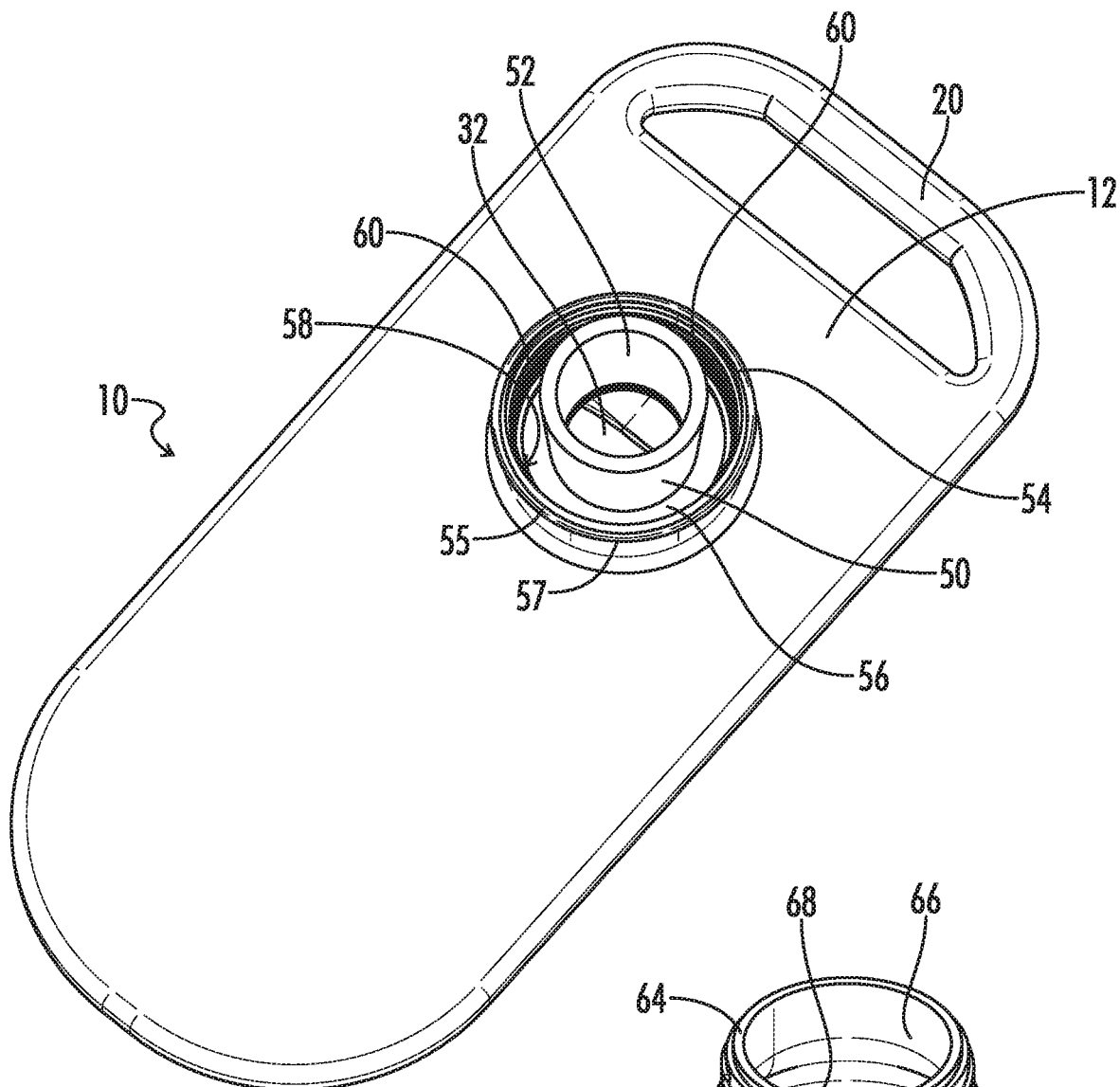
FIG. 5 illustrates a prospective bottom view of an embodiment of the device.
Figure 6:
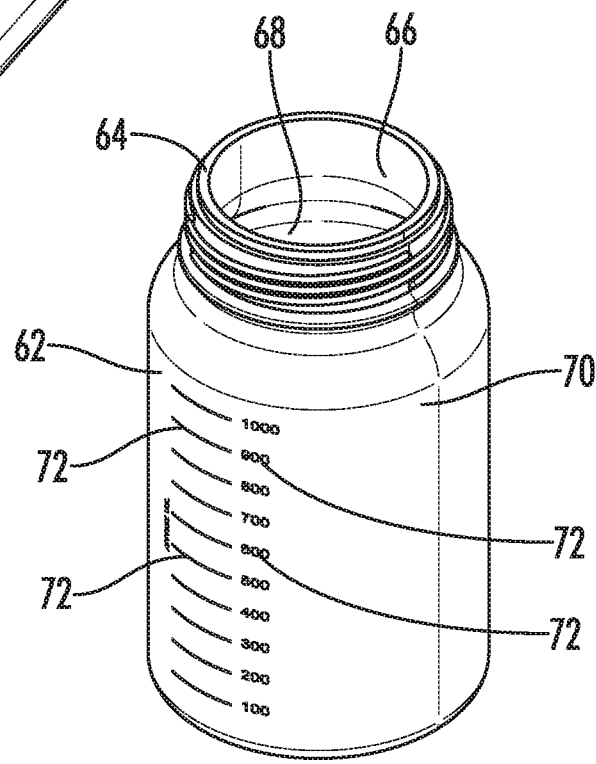
FIG. 6 illustrates a top perspective view of a container according to the embodiment of the device.
Figure 7:
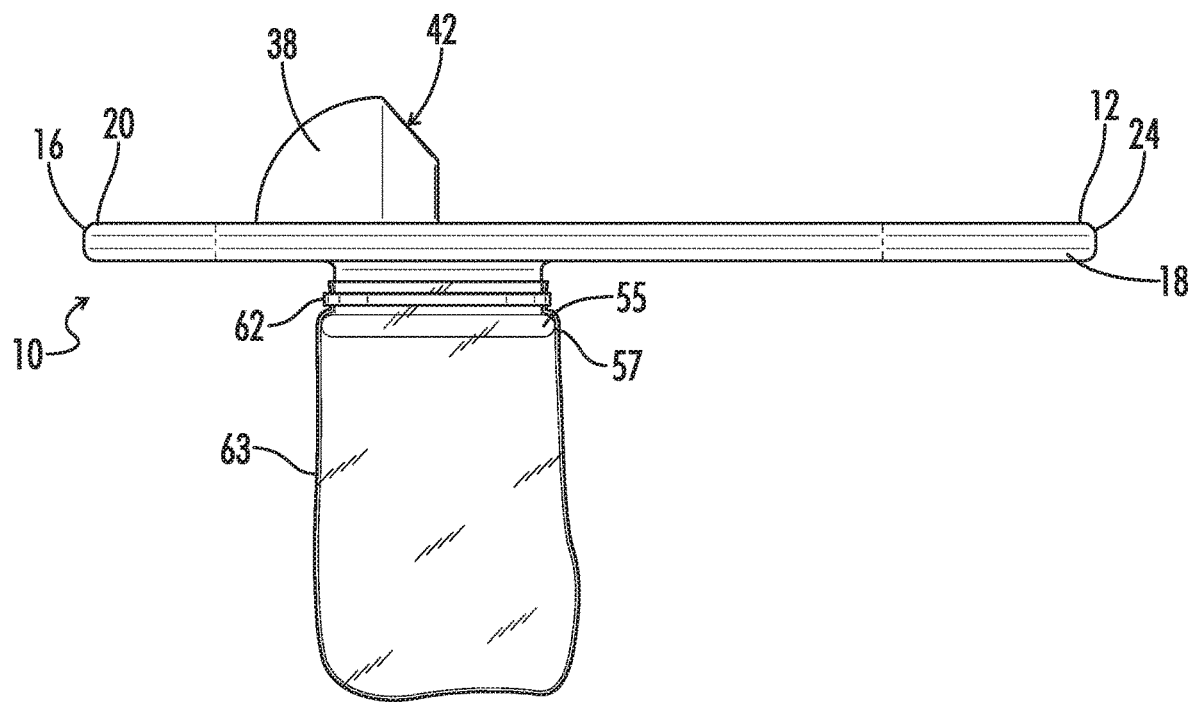
FIG. 7 illustrates an elevation view according to another embodiment of the device.
Figure 8:
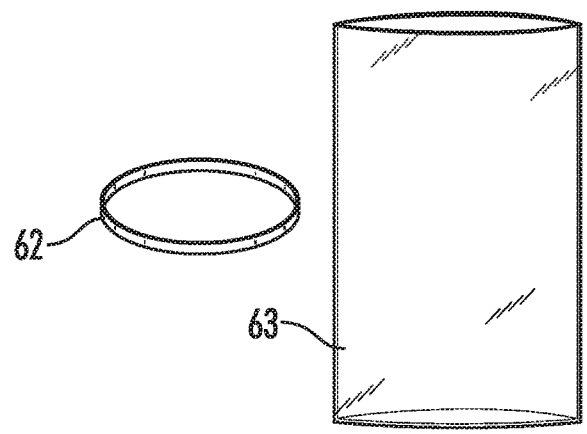
FIG. 8 illustrates a bag and a fastener of the embodiment of FIG. 7.

Referring to FIGS. 1-8, a device 10 for capturing and disposing of urine from a subject, such as a human, is disclosed. The subject may be male or female.

In an embodiment, the device 10 includes a rigid and elongated body 12. The elongated body 12 may be dimensioned such that it has a length that exceeds a width, such as a length that is 101-300% a width. The body 12 may be constructed of one or more metals, polymers, or any other suitable material(s). The elongated body 12 may include a top surface 14. When in use by a subject, the top surface 14 will be facing upwardly toward the subject such that gravity directs urine down to the top surface 14.

The device 10 may include a handle end 16 and a groin end 18 disposed opposite on the elongated body 12 from the handle end 16. When in use by a subject, the groin end 18 will face toward the subject and the handle end 16 will face away from the subject. The handle end 16 and the groin end 18 may be disposed lengthwise on the elongated body 12.

The device 10 may include a rigid handle 20. The handle 20 may be integrally formed with the elongated body 12. The handle 20 may be disposed at the handle end 16. The subject, or another person, may use the handle 20 to position the device 10 at the groin region of the subject such that the subject may urinate in the device 10. The handle 20 may curve outwardly from the handle end 10. An opening 21, or handle hole, may be disposed between and defined by the handle 20 and the handle end 16 of the device 10. The handle 20 and the device 10 may be integrally formed. All, or selectively any combination, of the elements of the device 10 herein may be integrally, or selectively separately, formed. The top surface 14 of the body 12 and a top surface 23 of the handle 20 may define a plane.

The groin end 18 may include a tapered profile 22. Beneficially, the tapered profile 22 may allow the device 10 to be positioned comfortably at the groin region of the subject, as the tapered profile 22 avoids sharp corners. The groin end 18 may include a curved edge 24. The curved edge 24 may allow the device 10 to be positioned comfortably at the groin region of the subject, as the curved edge 24 may form a "wedge-like" shape to wedge the groin end 18 of the device 10 between the subject and a surface (e.g., a bed surface or chair surface) on which the subject is laying or sitting.

The device 10 may comprise a groove 26, or indentation, disposed or formed in the top surface 14. The groove 26 may be elongated and extend at least partially lengthwise along the elongated body 12. The groove 26 may be defined by a continuously curved indentation in the top surface 14. The groove 26 may include an aperture end 28 and an urination end 30. The aperture end 28 may be disposed proximate to handle end 16 of the device 10, and the urination end 30 may be disposed on the groove 26 opposite from the aperture end 28 (e.g., proximate to the groin end 18 of the device 10). An aperture 32 may be disposed in the groove 26, such as at, or proximate to, the aperture end 28. The groove 26 may slope toward the aperture 32 such that liquid (e.g., urine) that is disposed in the groove 26 is directed toward the aperture 32.

The aperture 32 may be configured, or dimensioned, to securely receive a removable stopper 34. The stopper 34 may be releasably secured at least partially within the aperture 32 by, for example, a friction fit. The stopper 34 may be formed by a resiliently biased material, such as rubber. A top wall 36 may be disposed around the groove 26.

The device 10 may include a splashguard 38 disposed at least partially around the aperture 32. Advantageously, the splashguard 38 may prevent urine from escaping the groove 26 when the subject is urinating into the groove 26. The splashguard 38 may extend from the top surface of the body 12. The splashguard 38 may include an inner width 40, which may be defined by a width of the groove 26. The splashguard 38 may include a splashguard edge 42 that faces the groin end 18 of the device 10. The splashguard edge 42 may include a recess 44. Recess 44 may curve inwardly away from the groin end 18 and toward the handle end 16. A collar 48 may be disposed between the splashguard 38 and the aperture 32 such that the splashguard 38 is spaced a distance from the aperture 32. The splashguard 38 may have a substantially hemispherical profile.

The device 10 may comprise a bottom surface 46. The bottom surface 46 may be disposed on the device 10 such that it generally faces a direction that is opposite from a direction faced by the top surface 14. The bottom surface 46 may be defined by a substantially flat plane 46, which advantageously increases the ease within which the device 10 may be slid toward and away from the groin region of the subject.

An open neck 50 may extend from the bottom surface 46, the open neck 50 having a cavity 52 in fluid communication with the aperture 32. A sleeve 54 may extend from the bottom surface 46 and around the open neck 50. The open neck 50 may extend from the bottom surface 46 to a height that is greater than a height the sleeve 54 extends from the bottom surface 46. A gap 56 may be disposed between the open neck 50 and the sleeve 54. The gap 56 may have a constant gap width as the gap extends around the open neck 50.

The sleeve 54 may comprise an interior wall surface 58. One or more threads 60 may be disposed around the interior wall surface 58 of the sleeve 54. The device 10 may include a container 62 configured to be releasably secured with the device 10 to collect and store urine for disposal. The container 62 may be a disposable flexible bag or a rigid vessel. The container 62 may have an opening 64 having external threads 66 configured to cooperatively engage the one or more threads 60 of the sleeve 54. The opening 64 may be in fluid communication with a chamber 68 defined by sidewalls 70 of the container 62. The container 62 may be secured with the device 10 by, for example, a snapping mechanism (i.e., friction fit) or rotating the container 62 relative to the device 10 to engage or release cooperative threads 60, 66. The gap 56 may be configured or dimensioned such that the opening 64 of the container 62 is securely received within the gap 56. The container 62 may be integrally formed and may be constructed of an opaque, translucent, or clear material, such as a polymer or glass. The container 62 may include one or more measuring indicia (e.g., lines and corresponding fluid volume) 72 such that the urine collected in the container 62 may be measured. Advantageously, this allows for convenient measuring and tracking of urinated fluid, which may be helpful in determining whether the subject needs to intake more or less water.

The sleeve 54 may comprise an outer lip 55 that extends outwardly from the sleeve 54. The outer lip 55 may be disposed radially around the sleeve 54 and be positioned at, or proximate to, an edge 57 of the sleeve. The outer lip 55 is particularly advantageous in embodiments of the device 10 having the container 62 that is a bag, as the outer lip 55 may secure the container 62 with the sleeve 54. For example, the bag may be positioned over the outer lip 55 and sleeve 54 and fastened with a fastener 63 (such as a tie, by stretchable material, or a rubber band). In this example, the outer lip 55 secures the fastener, and thus the bag, from sliding off sleeve 54, especially as gravity exerts greater downward force on the bag when urine is collected.

The device 10 may be used with a composition for turning urine into a gelatin or solid to mask urine odor and/or eliminate spills. The composition may be added into the container 62 before or after urine is collected to solidify or gelatinize the collected urine. Such compositions are available from, for example, EMERGENCY ZONE of Orem, Utah as the ECO GEL product or RELIANCE PRODUCTS of Winnipeg, Canada as the BIO-GEL product.

Methods of using the device 10 described herein are disclosed. The device 10 may be positioned by positioning the groin end 18 at and underneath the groin region of the subject such that the groove 26 generally longitudinally extends from the groin region of the subject and the device is between the legs of the subject. The subject may be in a seated, a high or low Fowler's position, or a high or low semi-Flower's position (e.g., sitting up in bed). The device 10 may be positioned using the handle 20. The device 10 may be positioned in downward angle as it extends away from the subject to guide urine toward the aperture 32.

The subject may urinate into the groove 26 when the device 10 is in position. The urine flows toward the aperture 32, passing through the aperture 32. The urine may flow through the neck 50 and into an attached container 62. The stopper 34 may be releasably secured within the aperture 32 such that collected urine cannot pass back through the aperture 32. The stopper 34 may be removed such that additional urine can be collected, as the container 62 may be dimensioned to store urine from multiple urinations. The collected urine may be measured using the measuring indicia 72. The collected urine may be disposed of, such as by releasing the container 62 from the device 10 and empting the container 62 into a drain or a toilet.

Thus, although there have been described particular embodiments of the present invention of a new and useful Urine Capturing Device Having a Splashguard and Methods of Using Thereof, it is not intended that such references be construed as limitations upon the scope of this invention except as set forth in the following claims.

What is claimed is:

1. A device for capturing and disposing of urine, comprising:
   an elongated body including
      a top surface,
      a bottom surface,
      a handle end, and
      a groin end opposite of the handle end;
   an open neck extending from the bottom surface of the body in a direction away from the top surface;
   a groove disposed in the top surface along the elongated body, wherein the top surface includes a laterally extending wall circumferentially disposed around the groove, wherein the laterally extending wall has a curved edge disposed between the top surface and the bottom surface;
   an aperture disposed on the groove and in fluid communication with the open neck; and
   a splashguard extending from the top surface of the elongated body, the splashguard disposed at least partially around the aperture, and wherein the splashguard includes an edge facing the groin end, the edge including a recess.

2. The device of claim 1, wherein the open neck is configured to securely receive a container.

3. The device of claim 1, further comprising a sleeve extending around the open neck, the sleeve including one or more threads configured to cooperatively engage with one or more threads of a container.

4. The device of claim 3, wherein the sleeve comprises an interior wall surface, and wherein the one or more threads of the sleeve are disposed around the interior wall surface.

5. The device of claim 4, further comprising a gap disposed between the interior wall surface and the open neck.

6. The device of claim 1, further comprising a handle disposed at the handle end.

7. The device of claim 6, wherein the handle curves outwardly from the handle end.

8. The device of claim 7, wherein an opening is disposed between the handle and the handle end.

9. The device of claim 6, wherein the top surface of elongated body and a top surface of the handle define a plane.

10. The device of claim 1, wherein the groin end includes a tapered profile.

11. The device of claim 1, wherein the groin end includes a curved edge.

12. The device of claim 1, wherein the splashguard includes an inner width defined by a width of the groove.

13. The device of claim 1, wherein the splashguard has a hemispherical profile.

14. The device of claim 1, wherein the recess continuously curves inwardly.

15. The device of claim 1, wherein the aperture is configured to securely receive a removable stopper.

16. The device of claim 1, further comprising a removable stopper configured to be received at least partially in the aperture.

17. The device of claim 1, wherein the groove is defined by a continuously curved indentation in the top surface.

18. The device of claim 1, wherein the top surface of the elongated body is opposite of the bottom surface of the elongated body.

19. The device of claim 10, wherein the tapered profile is defined by the top surface sloping downwards towards the bottom surface of the device at the groin end.

20. The device of claim 1, wherein the bottom surface is defined by a substantially flat plane.

* * * * *